US011851392B2

(12) United States Patent
Sharpe et al.

(10) Patent No.: US 11,851,392 B2
(45) Date of Patent: Dec. 26, 2023

(54) SELF-CONDENSATION OF ALDEHYDES

(71) Applicant: EASTMAN CHEMICAL COMPANY, Kingsport, TN (US)

(72) Inventors: Robert Jacks Sharpe, Johnson City, TN (US); Scott Donald Barnicki, Kingsport, TN (US); Manik Lal Saha, Longview, TX (US); Kenneth Wayne Hampton, Jr., Gilmer, TX (US); Damon Ray Billodeaux, Longview, TX (US); Robert Thomas Hembre, Johnson City, TN (US)

(73) Assignee: Eastman Chemical Company, Kingsport, TN (US)

( * ) Notice: Subject to any disclaimer, the term of this patent is extended or adjusted under 35 U.S.C. 154(b) by 226 days.

(21) Appl. No.: 17/290,901

(22) PCT Filed: Oct. 31, 2019

(86) PCT No.: PCT/US2019/059034
§ 371 (c)(1),
(2) Date: May 3, 2021

(87) PCT Pub. No.: WO2020/101902
PCT Pub. Date: May 22, 2020

(65) Prior Publication Data
US 2021/0380508 A1 Dec. 9, 2021

Related U.S. Application Data

(60) Provisional application No. 62/760,128, filed on Nov. 13, 2018.

(51) Int. Cl.
*C07C 45/45* (2006.01)
*C07C 29/15* (2006.01)
*B01J 31/04* (2006.01)

(52) U.S. Cl.
CPC ............... *C07C 29/15* (2013.01); *B01J 31/04* (2013.01); *C07C 45/45* (2013.01)

(58) Field of Classification Search
CPC ........... C07C 45/45; C07C 29/15; B01J 31/04
See application file for complete search history.

(56) References Cited

U.S. PATENT DOCUMENTS

| | | | |
|---|---|---|---|
| 3,463,818 A | 8/1969 | Blumenthal | |
| 4,159,206 A | 6/1979 | Armbruster et al. | |
| 4,196,151 A | 4/1980 | Suyama et al. | |
| 4,408,079 A | 10/1983 | Merger et al. | |
| 4,496,770 A | 1/1985 | Duembgen et al. | |
| 5,162,552 A | 11/1992 | Merger et al. | |
| 9,822,053 B2 | 11/2017 | Boppana et al. | |
| 2011/0046420 A1 | 2/2011 | Kramarz et al. | |

FOREIGN PATENT DOCUMENTS

| | | |
|---|---|---|
| CH | 173737 A | 12/1934 |
| CN | 101830785 A | 9/2010 |
| CN | 102746129 A | 10/2012 |
| EP | 0013385 A1 | 7/1980 |
| SU | 1263693 A1 | 10/1986 |
| WO | WO 2018/034609 A1 | 2/2018 |

OTHER PUBLICATIONS

Notification of Transmittal of the International Search Report and the Written Opinion of the International Searching Authority with dated Feb. 24, 2020 for International Application No. PCT/US2019/059034.
Bruner, 3,3,5-Trimethylhexanol and Its Derivatives, Industrial and Engineering Chemistry, 1949, vol. 41, No. 12, pp. 2860-2864.
Bui, "A proline-catalyzed asymmetric Robinson annulation reaction", Tetrahedron Letters, 2000, vol. 41, pp. 6951-6954.
Ishikawa, et al., "Pyrrolidine Catalyzed Homo-Aldol Condensation Reaction of Aldehydes", Synlett, vol. 4, 1999, pp. 450-452.
Ostrowski, et al., "A comprehensive investigation and optimisation on the proteinogenic amino acid catalysed homo aldol condensation", Tetrahedron, 2016, 72, 592-598.
Seki, "Continuous catalytic "one-pot" multi-step synthesis of 2-ethylhexanal from crotonaldehyde" Chem Comm, 2007, pp. 3562-3564.
Wang, et al., "Total Synthesis of Scholancitrilactones B and C", Angewandte Chemie International Edition, 2015, 54, pp. 5732-5735.
Wilhelm, et al., "Uber Einige Aldolund Kondensationsreaktionen des Phenylacetaldehyds", Chemische Berichte, vol. 85, No. 12, 1952, pp. 1116-1119.
Zeidan, "The effect of acid-base pairing on catalysis: An efficient acid-base functionalized catalyst for aldol condensation" Journal of Catalysis, 2007, vol. 247, pp. 379-382.
Zhang "n-Butyraldehyde Self-Condensation Catalyzed by Sulfonic Acid Functionalized Ionic Liquids", IECR, 2014, vol. 53, pp. 16707-16714.

*Primary Examiner* — Sikarl A Witherspoon
(74) *Attorney, Agent, or Firm* — Steven A. Owen

(57) ABSTRACT

An efficient process useful for the self-condensation of aliphatic aldehydes is provided, catalyzed by dialkylammonium carboxylate salts. In particular, the invention provides a facile method for the preparation of 2-ethyl hexenal via the self-condensation of butyraldehyde using various dialkylammonium carboxylates, e.g., diisopropylammonium acetate or dimethylammonium acetate, as catalyst. Additionally, residual nitrogen arising from the catalyst can be reduced to ~100 ppm levels in the product via a simple washing procedure. The invention provides a process for preparing alkenals under conditions which limit the formation of undesired impurities and high-boiling oligomeric substances.

16 Claims, No Drawings

SELF-CONDENSATION OF ALDEHYDES

CROSS-REFERENCE TO RELATED APPLICATION(S)

This application is a national stage filing under 35 USC § 371 of International Application Number PCT/US2019/059034, filed on, Oct. 31, 2019 which claims the benefit of the filing date to U.S. Provisional Application No. 62/760,128, filed on Nov. 13, 2018, the entire disclosures of which are incorporated by reference herein.

FIELD OF THE INVENTION

This invention belongs to the field of organic chemistry. In particular, it relates to a process for preparing alkenals.

BACKGROUND OF THE INVENTION

2-Ethylhexanol (2EH) is a critically-important chemical in the preparation of various coatings, additives, and surfactants. The conventional process for preparing 2EH typically begins with hydroformylation of propylene to provide n-butyraldehyde. Self-condensation of n-butyraldehyde with basic catalysis affords 2-ethylhexenal (2EH Enal), which upon global hydrogenation, provides the 2EH. With regard to this conventional process, the conversion of n-butyraldehyde to 2EH Enal generally take place in the presence of catalytic amounts of sodium hydroxide. This process, however, suffers from significant drawbacks including the formation of higher-order oligomers or polymers, poor selectivity, and product color. Moreover, the use of sodium hydroxide requires treatment of highly basic wastewater. Thus, there is a need for improved techniques for making these desirable compounds.

SUMMARY OF THE INVENTION

The invention provides an efficient method for the self-condensation of aliphatic aldehydes, catalyzed by dialkylammonium carboxylate salts. The reaction is demonstrated using a variety of dialkylammonium salts as catalysts, and an analysis of the effectiveness of these catalysts under different conditions is presented below. Additionally, residual nitrogen arising from the catalyst can be reduced to –100 ppm levels in the product via a simple washing procedure. This process also provides the desired alkenal products under conditions which limit the formation of undesired impurities and high-boiling substances.

DETAILED DESCRIPTION

In a first embodiment, the invention provides a process for preparing an alkenal, comprising self-condensing an aliphatic aldehyde having at least 3 carbon atoms, in the presence of a catalyst comprising a dialkylammonium carboxylate salt, to produce the corresponding alkenal.

In a second embodiment, the invention provides a process for preparing an alkenal of the Formula (II)

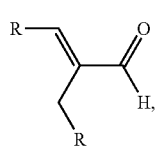

wherein R is chosen from phenyl, $C_1$-$C_{15}$ alkyl, or a group of the formula —$(CH_2)_n$-phenyl, wherein n is an integer of from 1 to 5, which comprises contacting a compound of the Formula (I)

with a dialkylammonium carboxylate salt.

In certain embodiments, the dialkylammonium carboxylate salts are chosen from dimethylammonium acetate, dimethylamonium propionate, dimethylammonium trifluoroacetate, dimethylammonium 2-ethylhexanoate, diethylammonium acetate, diethylammonium propionate, diethylammonium trifluoroacetate, diethylammonium 2-ethylhexanoate, pyrrolidine acetate, pyrrolidine propionate, pyrollidine trifluoroacetate, pyrrolidine 2-ethylhexenoate, diisopropylammonium acetate, diisopropylammonim propionate, diisopropylammonium trifluoroacetate, diisopropylammonium 2-ethylhexanoate, and dibenzylammonium acetate.

In another embodiment, the dialkylammonium carboxylate salt is a diisopropylammonium carboxylate salt. In a further embodiment, the dialkylammonium carboxylate salt is diisopropylammonium acetate.

In another embodiment, the dialkylammonium carboxylate salt is a dimethylammonium carboxylate salt. In a further embodiment, the dialkylammonium carboxylate salt is dimethylammonium acetate.

Examples of compounds of Formula (I) include n-butyraldehyde, propionaldehyde, octanal, lauric aldehyde, phenylacetaldehyde, hydrocinnamaldehyde, and the like.

The process of the invention may be conducted at atmospheric pressure and at ambient temperatures but may also be conducted at elevated temperature and pressures. Accordingly, in certain embodiments, the process is conducted from temperatures of from about 23° C. to about 160° C., about 65° C. to about 110° C., about 70° C. to about 95° C., or about 30° C. to about 140° C. In certain embodiments, the process is conducted at pressures of about 1 atmosphere to about 30 psi or about 1 atmosphere to about 40 psi.

As noted herein, residual impurities may be easily removed via washing the product of the invention with dilute alkanoic acid such as acetic acid. Accordingly, in a further embodiment, the invention provides the above process, further comprising the step of washing the resulting alkenal with a dilute aqueous alkanoic acid. Advantageously, the alkanoic acid is chosen to coincide with the carboxylate moiety on the dialkylammonium carboxylate catalyst to allow for regeneration of same. So, for example, when the catalyst is diisopropylammonium acetate, the alkanoic acid utilized in this washing step is advantageously chosen to be acetic acid.

In a further embodiment, the invention provides a process for preparing 2-ethyl-hexenal, which comprises contacting n-butyraldehyde with diisopropylammonium acetate to form 2-ethyl-hexenal. In a further embodiment, the process is conducted at a temperature of about 23° C. to about 160°. In a further embodiment, the process is conducted at a temperature of about 65° C. to about 110° C. or a temperature of about 70-95° C., and at a pressure of about 1 atmosphere to about 30 psi. In yet a further embodiment, the 2-ethylhexenal product is washed with dilute acetic acid.

In a further embodiment, the invention provides a process for preparing 2-ethyl-hexenal, which comprises contacting n-butyraldehyde with diisopropylammonium acetate or dimethylammonium acetate. In a further embodiment, the process is conducted at a temperature of about 23° C. to about 160° C. or about 30° to about 140° C. In a further embodiment, the process is conducted at a temperature of about 120° to about 130° C., or about 125° C. with various molar equivalents of catalyst loading, for example, from about 5 mole percent to about 40 mole percent.

In a further embodiment, the enal product of the invention is subjected to hydrogenation to provide the corresponding aliphatic alcohol. Accordingly, in a further aspect of the invention, there is provided the process as recited above, further comprising the step of hydrogenation. In one aspect, the hydrogenation step involves the hydrogenation of 2-ethylhexenal, to afford 2-ethyl hexanol. Standard conditions of temperature, pressure, presence of hydrogen, and a hydrogenation catalyst such as palladium on carbon, platinum on carbon, or Raney Nickel can be utilized.

EXPERIMENTAL SECTION

Nitrogen Analysis by CHN:

Nitrogen results were obtained using a Flash EA1112 instrument. The instrument was calibrated using an Atropine standard. Atropine was analyzed as a known standard with carbon, hydrogen, and nitrogen components and also as an unknown to check the calibration. Retention times were adjusted based on this calibration. Sample analysis was performed using a sample size of approximately 5 mg. The sample was weighed into a sample tin and placed into the instrument auto-sampler. The sample sequence began with a blank, atropine, blank, and samples. Samples were analyzed in duplicate with blanks between each sample. Each sequence ended with Atropine and a blank. The auto-sampler dropped the sample tin into the combustion/reactor tube. The sample was combusted with oxygen and converted to the gas phases, then carried to a GC column by helium where each component was separated. The carbon, hydrogen, and nitrogen peaks were displayed on a chromatogram. Component results were reported at percent level.

Gas Chromatography for 2-Ethyl-Hexanol (2EH)

Samples were chromatographed on a Shimadzu 2010 equipped with a heated split injector, a DB-WAXetr column, and a flame ionization detector (FID). The concentrations of sample components were calculated from the integrated chromatogram using internal standard quantitation. The software used for both acquisition and data processing was EZChrom Elite, V. 3.3.2.SP2.

Samples from 300 mL autoclave experiments were chromatographed on a Agilent 6890N equipped with a heated split/splitless injector, a RTX1 column, and a flame ionization detector (FID). The concentrations of sample components were calculated from the integrated chromatogram reported as area percentage. The software used for both acquisition and data processing was Chemstation B.04.03.

UV/Vis Characterization:

Ultraviolet/Visible spectrum data were collected using a Perkin Elmer Lambda 35. The range was set to 360-780 nm with 1 nm slit width and a scan speed of 240 nm/min. The spectral data was collected on neat samples analyzed in a low-volume 50 mm cell with Millipore water used to blank the instrument. Samples with a higher viscosity were heated at 60 Celsius for 10 minutes before collecting data. The organic portion in samples that contained both an organic and aqueous layer was analyzed. Spectral data were then imported into Easy Match QC v4.87 software to generate L*, a*, b*, APHA and Gardner values. Visible spectrometers are utilized to collect spectra for color evaluation according to ASTM E1164. Tristimulus and CIE L*, a*, and b* are calculated according to ASTM E308.

Sample Procedure for the Self-Condensation of Butyraldehyde Using Varied Catalysts from Table 1.

A 20 mL scintillation vial was charged with a magnetic stirring bar. The vial was then charged with water (0.9 mL) followed by diisopropylamine (3.37 g). Propionic acid (2.47 g) was then added dropwise to the vial with stirring, resulting in an exotherm. The solution was allowed to cool to room temperature with stirring whereupon n-butyraldehyde (6 g) was added dropwise. The vial was sealed, and the mixture was heated to 70° C. and stirred for 3 hours. During this time period, the reaction mixture gradually became a biphasic solution. At the end of the three hours, the reaction mixture was allowed to cool to room temperature. The upper organic layer was removed via syringe, and the product was analyzed via GC analysis, nitrogen content, and product color.

Following the general procedure described above, all of the samples in table 1 were prepared.

Sample Procedure for the Self-Condensation of Butyraldehyde Using Diisopropylammonium Acetate (DIPA-OAc) Concomitant with Product Washing with Acetic Acid (AcOH).

A 20-mL scintillation vial was charged with a magnetic stirring bar. The vial was then charged with water (0.9 mL) followed by diisopropylamine (3.37 g). Acetic acid (1 g) was then added dropwise to the vial with stirring, resulting in an exotherm. The solution was allowed to cool to room temperature with stirring whereupon n-butyraldehyde (6 g) was added dropwise. The vial was sealed, and the mixture was heated to 85° C. and stirred for 6 hours. During this time period, the reaction mixture gradually became a biphasic solution. At the end of the 6 hours, the reaction mixture was allowed to cool to room temperature. The upper organic layer was removed via syringe and transferred to a separate 20-mL scintillation vial. A 0.25 mL aliquot was removed and used to analyze for product content, residual nitrogen, and product color. This material was determined to contain 93.9% 2EH Enal by GC analysis and 1.85% residual nitrogen by CHN analysis. a* was measured to be −5.79, and b* was measured to be 22.16. To the remaining material was charged an equal volume solution of 10% v/v AcOH (aq.), and the biphasic mixture was allowed to stir for 10 minutes. Following this time period, the organic layer was removed by syringe, and the product was analyzed via GC analysis, nitrogen content, and product color. This material was determined to contain 90% 2EH Enal by GC analysis and 105 ppm residual nitrogen by CHN analysis. a* was measured to be −3.35, and b* was measured to be 11.79.

Sample Procedure for the Self-Condensation of Various Aldehydes Using DIPA-OAc.

A 20-mL scintillation vial was charged with a magnetic stirring bar. The vial was then charged with water (0.45 mL) followed by diisopropylamine (3.37 g). Acetic acid (0.5 g) was then added dropwise to the vial with stirring, resulting in an exotherm. The solution was allowed to cool to room temperature with stirring whereupon n-octanal (5.33 g) was added dropwise. The vial was sealed, and the mixture was heated to 85° C. and stirred for 6 hours. During this time period, the reaction mixture gradually became a biphasic solution. At the end of the 6 hours, the reaction mixture was allowed to cool to room temperature. The upper organic layer was removed via syringe and transferred to a separate 20-mL scintillation vial. This material was determined to contain 95.94% enal and 4.06% recovered starting material by quantitative GC_MS analysis. Residual nitrogen content of the unwashed material was 1.05% by CHN analysis; a* was measured to be −1.44, and b* was measured to be 11.25. Following the general procedure described above, all of the samples in table 3 were prepared.

Sample Procedure for the 1 L Self-Condensation of n-Butyraldehyde Using DIPA-OAc with Elevated Temperature and Pressure.

A 1 L glass jar was charged with water (45.0 g), diisopropylamine (168 g), and a magnetic stirring bar. The stirring was started, and acetic acid (100 g) was added dropwise, resulting in an exothermic reaction. The mixture was allowed to cool to room temperature whereupon butyraldehyde (300 g) was added to the mixture dropwise with vigorous stirring. The mixture was then transferred to an autoclave. The autoclave was purged twice with nitrogen and then subsequently pressurized to 30 psi N2. Agitation was set to 800 rpm, and the mixture was gradually heated to 95° C. Once the internal reaction temperature reached 75° C., the reaction mixture was sampled for completeness via GC analysis. Sampling was carried out every 5 minutes until a hold time of 1 hour was completed. The autoclave was then cooled to room temperature, and the final reaction mixture was sampled for completeness via GC analysis.

Following the general procedure described above, the samples in tables 4-8 were generated.

Sample Procedure for the 300 mL Self-Condensation of n-Butyraldehyde Using DMA-OAc (Dimethylammonium Acetate) with Elevated Temperature and Pressure.

A 250 mL three-neck round-bottom flask was charged with 55.0 gm of 40% aqueous solution of DMA (Dimethylamine) and a magnetic stirring bar and cooled 0° C. using an ice bath. The stirring was started, and 29.3 gm glacial acetic acid was added a rate of 2 mL/min using a dropping funnel. The reaction temperature was maintained at about 30° C. throughout the reaction. After completing the addition, the mixture was stirred for an additional 5 min at room temperature and was then slowly transferred into a 300 mL autoclave containing 160 gm of n-butyraldehyde. The autoclave was pressurized to 40 psi N2. Agitation was set to 900 rpm, and the mixture was gradually heated to 125° C. The reaction mixture was sampled when the onset reached and then every 30 mins for a period of 2 hours.

Following the general procedure described above, the samples in tables 9-11 were generated.

In the examples below, we employed each catalyst at 40 mol % relative to the aldehyde and ran the experiment for 3 hours at 70° C. Table 1 summarizes the catalysts examined.

TABLE 1

Synthesis of 2EH Enal from Butyraldehyde Using Varied Dialkylammonium Catalysts.

| Example | Amine (Equiv) | Acid (Equiv) | Catalyst Name | % nBuCHO | % 2EH Enal | % impurities and byproducts | Residual Nitrogen | a* | b* |
| --- | --- | --- | --- | --- | --- | --- | --- | --- | --- |
| 1 | HNMe2 (0.4) | AcOH (0.4) | Dimethylammonium acetate | 0.90% | 93.46% | 5.63% | 3746 ppm | −7.13 | 60.75 |
| 2 | HNMe2 (0.4) | PrOH (0.4) | Dimethylammonium propionate | 0.29% | 94.49% | 5.23% | 4120 ppm | −8.86 | 57.57 |
| 3 | HNMe2 (0.4) | TFA (0.4) | Dimethylammonium trifluoroacetate | 29.58% | 38.03% | 32.39% | 3504 ppm | −11.46 | 54.67 |
| 4 | HNMe2 (0.4) | 2EH Acid (0.4) | Dimethylammonium 2-ethylhexanoate | 0.02% | 93.88% | 6.10% | 5030 ppm | −2.57 | 83.02 |
| 5 | HNEt2 (0.4) | AcOH (0.4) | Diethylammonium acetate | 0.40% | 96.08% | 3.52% | 4652 ppm | 32.39 | 112.91 |
| 6 | HNEt2 (0.4) | PrOH (0.4) | Diethylammonium propionate | 0.17% | 93.63% | 6.20% | 7138 ppm | 30.76 | 112.84 |
| 7 | HNEt2 (0.4) | TFA (0.4) | Diethylammonium trifluoroacetate | 47.70% | 7.02% | 45.27% | 6586 ppm | 37.98 | 91.05 |
| 8 | HNEt2 (0.4) | 2EH Acid (0.4) | Diethylammonium 2-ethylhexanoate | 0.25% | 90.00% | 9.74% | 6746 ppm | 52.3 | 101.79 |
| 9 | Pyrrolidine (0.4) | AcOH (0.4) | Pyrrolidinium acetate | 0.05% | 92.72% | 7.24% | N/A | 37.62 | 14.95 |
| 10 | Pyrrolidine (0.4) | PrOH (0.4) | Pyrrolidinium propionate | 0.05% | 86.31% | 13.64% | 1.55% | 35.99 | 12.2 |
| 11 | Pyrrolidine (0.4) | TFA (0.4) | Pyrrolidinium trifluoroacetate | 1.94% | 92.41% | 5.65% | 1.22% | N/A* | N/A |
| 12 | Pyrrolidine (0.4) | 2EH Acid (0.4) | Pyrrolidinium 2-ethylhexanoate | 0.05% | 72.95% | 27.00% | 2.09% | 21.79 | 5.79 |
| 13 | Diisopropylamine (0.4) | AcOH (0.4) | Diisopropylammonium acetate | 3.20% | 82.85% | 13.95% | 1.85% | −4.92 | 17.54 |
| 14 | Diisopropylamine (0.4) | AcOH (0.4) | Diisopropylammonium acetate | 0.8% | 93.9% | 5.2% | <1.0% | −5.79 | 22.16 |
| 15 | Diisopropylamine (0.4) | PrOH (0.4) | Diisopropylammonium propionate | 6.91% | 84.81% | 8.27% | 2427 ppm | 35.99 | 12.2 |
| 16 | Diisopropylamine (0.4) | TFA (0.4) | Diisopropylammonium trifluoroacetate | 54.18% | 1.40% | 44.43% | 1.48% | −1.33 | 4.32 |
| 17 | Diisopropylamine (0.4) | 2EH Acid (0.4) | Diisopropylammonium 2-ethylhexanoate | 7.21% | 49.63% | 43.15% | 1.51% | −3.97 | 10.2 |

TABLE 1-continued

Synthesis of 2EH Enal from Butyraldehyde Using Varied Dialkylammonium Catalysts.

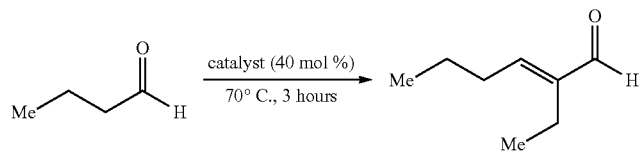

| Example | Amine (Equiv) | Acid (Equiv) | Catalyst Name | % nBuCHO | % 2EH Enal | % impurities and byproducts | Residual Nitrogen | a* | b* |
|---|---|---|---|---|---|---|---|---|---|
| 18 | Dibenzylamine (0.4) | AcOH (0.4) | Dibenxylammonium acetate | 0.22% | 91.05% | 8.73% | 2.40% | 3.3 | 104.05 |
| 19 | Triethylamine (0.4) | AcOH (0.4) | Triethylammonium acetate | 84.25% | 9.09% | 6.67% | 725 ppm | −1.16 | 10.15 |
| 20 | none | Tryptophan | | 0.41% | 95.92% | 3.67% | 3589 ppm | 0.42 | 0.42 |
| 21 | | TFA (0.4) | Dibenzylammonium trifluoroacetate | 10.36% | 30.94% | 58.71% | 3.15% | 6.19 | 121.4 |
| 22 | Butylamine (0.4) | AcOH (0.4) | Butylammonium acetate | 0.14% | 42.02% | 57.85% | 4.25% | N/A | N/A |

*Reaction Conditions: 85° C., 6 hours
product content measure by GC Analysis
product color measured by UV-Vis analysis
residual nitrogen measured via CHN analysis or total nitrogen analysis In considering the highest performing catalyst of this series, we noted that while diisopropylammonium acetate (DIPA-OAc) failed to give complete conversion of butyraldehyde, the reaction proceeded with minimal formation of byproducts and sample color. Furthermore, when the reaction was carried out at 85° C. for six hours, we observed near complete conversion of the aldehyde to the enal, again with minimal color or byproducts. As comparative examples, dibenzylammonium trifluoroacetate gave low product formation in addition to significant product color. Additionally, tryptophan gave promising levels of product formation, but the anticipated cost of this catalyst would likely preclude its use in industrial operations.

An important consideration in the use of amine-based catalysts is the ability to remove residual nitrogen from the product. Indeed, direct isolation of 2-ethyl hexenal (2EH enal) produced from the title catalyst afforded the product comprising ~1% nitrogen by CHN analysis (Table 2). After further experimentation, however, we learned that residual nitrogen in the product material could be reduced to ppm concentrations via simple washing of the product with dilute aqueous acetic acid. Additionally, we found that this washing procedure further reduced product color.

TABLE 2

Reduction of residual nitrogen content in 2EH Enal produced via iminium catalysis.

| Example | Purification Method | % Enal | % Starting Material | % Other Products | Nitrogen Content | a* | b* |
|---|---|---|---|---|---|---|---|
| 23 | None | 93.9 | 0.8 | 5.2 | 1.85% | −5.79 | 22.16 |
| 24 | Wash with 10% (aq.) AcOH | 90.0 | 1.6 | 8.4 | 105 ppm | −3.35 | 11.92 | product content measure by GC Analysis
product color measured by UV-Vis analysis
residual nitrogen measured via CHN analysis or total nitrogen analysis The following experiments illustrate the ability of the catalysts of the invention to promote the self-condensation of alternative aliphatic aldehydes. As seen from the table, the DIPA-OAc catalyst effectively promoted the formation of all aldehydes examined with the exception of acetaldehyde, which gave primarily a mixture of oligomeric products. Notably, in the case of aldehydes more sterically-encumbering that butyraldehyde, the catalyst performed exceptionally, delivering the corresponding condensation products in high purity.

TABLE 3

Homo-Aldolization of Various Aldehydes using the DIPA-OAc Catalyst

| Example | Aldehyde | % Enal | % Starting Material | % Other Products | % Nitrogen | a* | b* |
|---|---|---|---|---|---|---|---|
| 25 | Acetaldehyde | 0 | 0 | N/A | 1.08 | 0.59 | 0.1 |
| 26 | Propionaldehyde | 81.55 | 0 | 18.44 | 1.35 | 7.97 | 88.52 |
| 27 | Octanal | 95.94 | 4.06 | 0 | 1.05 | −1.44 | 11.25 |
| 28 | Lauric Aldehyde | 92.87 | 7.13 | 0 | <1.0 | −1.31 | 10.36 |
| 29 | Phenylacetaldehyde | 95.09 | 2.16 | 2.75 | N/A | 27.63 | 65.66 |
| 30 | Hydrocinnamaldehyde | 97.61 | 0.81 | 1.58 | N/A | 48.22 | 66.52 | product content measure by GC Analysis
product color measured by UV-Vis analysis
residual nitrogen measured via CHN analysis or total nitrogen analysis The following experiments were carried out in pressurized autoclaves. Accordingly, we carried out the condensation of butyraldehyde at varying temperatures and catalyst loadings at 30 psi and collected information on the reaction rate via periodic sampling. These experiments are detailed in tables 4-8. Collectively, these experiments demonstrate that the reaction rate can be significantly enhanced by carrying out the reaction at elevated temperature and pressure. Notably, by-product formation is minimized at reaction temperatures below 115° C. Additionally, the catalyst loading may be lowered to 20 mol % without significant reduction in reaction rate. These experiments further illustrate the ability of DIPA-OAc to deliver 2EH Enal in good purity at commercially relevant reaction rates.

TABLE 4

1 L scale aldolization of butyraldehyde using 40 mol % catalyst at 105° C.

| Temperature | Time minutes | n-Butyraldehyde 0.01 | n-Butanol 0.01 | 2-Ethylhexenal 0.01 | n-Butyric Acid 0.01 | Unknowns 0.01 |
|---|---|---|---|---|---|---|
| 75.1 | 0 | 44.48% | 0.07% | 27.75% | 2.18% | 25.51% |
| 79.6 | 5 | 38.08% | 0.07% | 37.84% | 1.23% | 22.79% |
| 84.3 | 10 | 32.08% | 0.05% | 46.24% | 1.10% | 20.53% |
| 88.5 | 15 | 23.04% | 0.04% | 64.82% | 0.82% | 11.27% |
| 92.5 | 20 | 16.82% | 0.04% | 75.37% | 0.59% | 7.19% |
| 96.3 | 25 | 11.36% | 0.04% | 84.32% | 0.39% | 3.90% |
| 99.4 | 30 | 8.98% | 0.04% | 87.93% | 0.30% | 2.75% |
| 101.3 | 35 | 7.64% | 0.04% | 89.82% | 0.25% | 2.25% |
| 102 | 40 | 6.77% | 0.01% | 90.77% | 0.28% | 2.17% |
| 102.6 | 45 | 6.60% | 0.02% | 91.50% | 0.25% | 1.63% |
| 104.1 | 50 | 5.90% | 0.03% | 92.01% | 0.27% | 1.79% |
| 105.2 | 55 | 5.50% | 0.01% | 92.15% | 0.27% | 2.06% |
| 105.3 | 60 | 5.40% | 0.03% | 92.62% | 0.28% | 1.68% |
| 104.7 | 65 | 4.98% | 0.03% | 93.00% | 0.29% | 1.70% |
| 104.3 | 70 | 4.76% | 0.03% | 92.86% | 0.29% | 2.06% |
| 104.2 | 75 | 4.68% | 0.02% | 93.40% | 0.28% | 1.62% |
| 105 | 80 | 4.31% | 0.03% | 93.55% | 0.30% | 1.81% |
| 105.6 | 85 | 4.17% | 0.01% | 93.69% | 0.31% | 1.82% |
| 105.7 | 90 | 3.94% | 0.03% | 94.02% | 0.31% | 1.70% |
| 105.4 | 95 | 3.76% | 0.03% | 94.12% | 0.32% | 1.78% |
| 105 | 100 | 3.63% | 0.01% | 94.22% | 0.32% | 1.83% |
| 105 | 105 | 3.64% | 0.02% | 94.06% | 0.31% | 1.97% |
| 105.4 | 110 | 3.41% | 0.02% | 94.03% | 0.32% | 2.22% |
| 105.6 | 115 | 3.24% | 0.02% | 94.22% | 0.33% | 2.19% | product content measured by GC Analysis

TABLE 5

1 L scale aldolization of butyraldehyde using 40 mol % catalyst at 95° C.

| Temperature | Time minutes | n-Butyraldehyde 0.01 | n-Butanol 0.01 | 2EHenal 0.01 | n-HOBu 0.01 | Unknowns 0.01 |
|---|---|---|---|---|---|---|
| 75 | 0 | 55.63% | 0.05% | 24.96% | 0.84% | 18.53% |
| 78.6 | 5 | 51.20% | 0.41% | 30.69% | 0.84% | 16.86% |
| 82 | 10 | 44.47% | 0.42% | 40.18% | 0.76% | 14.16% |
| 85.1 | 15 | 36.65% | 0.45% | 49.35% | 0.71% | 12.84% |
| 87.6 | 20 | 32.00% | 0.45% | 59.13% | 0.54% | 7.88% |
| 89.6 | 25 | 21.59% | 0.46% | 71.58% | 0.45% | 5.92% |
| 91.3 | 30 | 16.80% | 0.44% | 78.12% | 0.36% | 4.28% |
| 93.1 | 35 | 13.13% | 0.43% | 82.78% | 0.30% | 3.35% |
| 95 | 40 | 10.35% | 0.40% | 85.98% | 0.28% | 2.99% |
| 96.1 | 45 | 8.45% | 0.36% | 88.66% | 0.23% | 2.30% |
| 96.1 | 50 | 7.21% | 0.35% | 90.06% | 0.20% | 2.18% |
| 96.1 | 55 | 6.38% | 0.33% | 91.23% | 0.20% | 1.86% |
| 95.7 | 60 | 5.89% | 0.30% | 91.84% | 0.19% | 1.77% |
| 94.9 | 65 | 5.37% | 0.30% | 92.41% | 0.19% | 1.73% |
| 95.2 | 70 | 5.08% | 0.29% | 92.76% | 0.19% | 1.67% |
| 95.6 | 75 | 4.74% | 0.01% | 93.12% | 0.19% | 1.94% |
| 95.6 | 80 | 4.51% | 0.01% | 93.36% | 0.19% | 1.93% |
| 95.8 | 85 | 4.29% | 0.01% | 93.62% | 0.19% | 1.89% |
| 96.2 | 90 | 4.15% | 0.02% | 93.75% | 0.19% | 1.89% |
| 96.7 | 95 | 3.99% | 0.01% | 93.94% | 0.19% | 1.87% | product content measured by GC Analysis

TABLE 6

1 L scale aldolization of butyraldehyde using 40 mol % catalyst at 115° C.

| Temperature | Time minutes | n-Butyraldehyde 0.01 | n-Butanol 0.01 | 2EHenal 0.01 | n-HOBu 0.01 | Unknowns 0.01 |
|---|---|---|---|---|---|---|
| 75.4 | 0 | 60.35% | 0.37% | 20.03% | 1.02% | 18.22% |
| 85.1 | 5 | 51.07% | 0.42% | 30.91% | 0.93% | 16.67% |
| 90.7 | 10 | 39.25% | 0.42% | 49.59% | 0.73% | 10.01% |
| 94.3 | 15 | 26.99% | 0.40% | 66.31% | 0.52% | 5.79% |
| 97.9 | 20 | 18.08% | 0.35% | 77.39% | 0.37% | 3.80% |
| 102.8 | 25 | 12.94% | 0.34% | 84.03% | 0.26% | 2.43% |
| 106.9 | 30 | 10.71% | 0.29% | 86.84% | 0.21% | 1.95% |
| 109 | 35 | 9.46% | 0.25% | 88.36% | 0.19% | 1.74% |
| 109.9 | 40 | 8.49% | 0.22% | 89.65% | 0.19% | 1.45% |
| 110.9 | 45 | 7.79% | 0.20% | 90.23% | 0.18% | 1.60% |
| 112.4 | 50 | 7.23% | 0.18% | 91.04% | 0.19% | 1.36% |
| 113.9 | 55 | 6.56% | 0.15% | 91.55% | 0.10% | 1.64% |
| 114.8 | 60 | 6.10% | 0.14% | 92.12% | 0.19% | 1.45% |
| 115.1 | 65 | 5.64% | 0.13% | 92.62% | 0.19% | 1.42% |
| 114.6 | 70 | 5.19% | 0.12% | 93.07% | 0.11% | 1.50% |
| 114.3 | 75 | 4.83% | 0.01% | 93.30% | 0.20% | 1.66% |
| 114.9 | 80 | 4.52% | 0.01% | 93.61% | 0.20% | 1.66% |
| 115.7 | 85 | 4.23% | 0.01% | 93.90% | 0.21% | 1.65% |
| 116.3 | 90 | 3.97% | 0.02% | 94.14% | 0.13% | 1.74% |
| 115.9 | 95 | 3.71% | 0.02% | 94.39% | 0.21% | 1.67% | product content measured by GC Analysis

TABLE 7

1 L scale aldolization of butyraldehyde using 30 mol % catalyst at 105° C.

| Temperature | Time minutes | n-Butyraldehyde 0.01 | n-Butanol 0.01 | 2EHenal 0.01 | n-HOBu 0.01 | Unknowns 0.01 |
|---|---|---|---|---|---|---|
| 86.5 | 5 | 26.25% | 0.04% | 53.22% | 1.14% | 19.35% |
| 89.6 | 10 | 14.42% | 0.04% | 69.35% | 1.07% | 15.12% |
| 91.9 | 15 | 17.51% | 0.02% | 71.20% | 0.84% | 10.42% |
| 94.3 | 20 | 13.89% | 0.02% | 78.34% | 0.67% | 7.08% |
| 96.8 | 25 | 10.47% | 0.02% | 84.05% | 0.51% | 4.95% |
| 99.1 | 30 | 7.97% | 0.02% | 88.03% | 0.42% | 3.57% |
| 101.8 | 35 | 7.07% | 0.02% | 90.40% | 0.37% | 2.13% |
| 104.8 | 40 | 6.10% | 0.02% | 91.40% | 0.33% | 2.15% |
| 106 | 45 | 6.34% | 0.02% | 91.52% | 0.30% | 1.82% |
| 106.1 | 50 | 6.19% | 0.01% | 91.83% | 0.29% | 1.68% |
| 105.8 | 55 | 5.72% | 0.01% | 92.37% | 0.27% | 1.63% |
| 105.7 | 60 | 5.82% | 0.02% | 92.15% | 0.28% | 1.72% |
| 105.7 | 65 | 5.34% | 0.02% | 92.65% | 0.28% | 1.72% |
| 105.6 | 70 | 5.46% | 0.01% | 92.64% | 0.27% | 1.61% |
| 106 | 75 | 4.98% | 0.02% | 92.96% | 0.28% | 1.76% |
| 106.2 | 80 | 4.95% | 0.00% | 93.19% | 0.27% | 1.59% |
| 106.3 | 85 | 4.81% | 0.00% | 93.18% | 0.27% | 1.74% |
| 106.1 | 90 | 4.64% | 0.01% | 93.34% | 0.28% | 1.72% |
| 105.7 | 95 | 4.38% | 0.00% | 93.68% | 0.28% | 1.66% | product content measured by GC Analysis

TABLE 8

1 L scale aldolization of butyraldehyde using 20 mol % catalyst at 105° C.

| Temperature | Time | n-Butyraldehyde 0.01 | n-Butanol 0.01 | 2EHenal 0.01 | 2EHOH 0.01 | n-HOBu 0.01 | Unknowns 0.01 |
|---|---|---|---|---|---|---|---|
| 75 | 0 | 50.24% | 0.00% | 18.59% | 1.77% | 2.08% | 27.32% |
| 80.7 | 5 | 46.95% | 0.00% | 26.39% | 1.19% | 1.93% | 23.54% |
| 85.8 | 10 | 38.95% | 0.00% | 40.76% | 0.74% | 1.71% | 17.85% |
| 90 | 15 | 34.48% | 0.00% | 49.36% | 0.56% | 1.56% | 14.03% |
| 93.8 | 20 | 24.96% | 0.00% | 65.14% | 0.00% | 1.17% | 8.73% |
| 96.8 | 25 | 21.86% | 0.00% | 70.58% | 0.00% | 0.93% | 6.63% |
| 99.5 | 30 | 18.10% | 0.00% | 76.50% | 0.00% | 0.77% | 4.63% |
| 101.3 | 35 | 15.09% | 0.00% | 81.04% | 0.00% | 0.62% | 3.25% |
| 102.4 | 40 | 12.99% | 0.00% | 83.89% | 0.00% | 0.54% | 2.58% |
| 103 | 45 | 11.89% | 0.00% | 85.63% | 0.00% | 0.44% | 2.04% |
| 103.8 | 50 | 12.31% | 0.00% | 85.07% | 0.00% | 0.43% | 2.18% |
| 104.4 | 55 | 11.31% | 0.00% | 86.79% | 0.00% | 0.38% | 1.52% |
| 104.1 | 60 | 10.71% | 0.00% | 87.33% | 0.00% | 0.38% | 1.58% |
| 103.7 | 65 | 9.23% | 0.01% | 88.80% | 0.00% | 0.35% | 1.60% |
| 105.1 | 70 | 9.64% | 0.00% | 88.66% | 0.00% | 0.34% | 1.37% |
| 106.1 | 75 | 8.34% | 0.01% | 89.71% | 0.00% | 0.36% | 1.57% |
| 105.6 | 80 | 8.46% | 0.01% | 89.71% | 0.00% | 0.34% | 1.48% |
| 104.9 | 85 | 8.50% | 0.02% | 89.55% | 0.00% | 0.35% | 1.58% |
| 104.8 | 90 | 8.49% | 0.01% | 89.66% | 0.00% | 0.33% | 1.50% |
| 104.9 | 95 | 7.38% | 0.00% | 90.59% | 0.00% | 0.32% | 1.71% |
| 104.9 | 100 | 7.63% | 0.00% | 90.74% | 0.00% | 0.31% | 1.32% |
| 105.1 | 105 | 7.35% | 0.00% | 91.05% | 0.00% | 0.30% | 1.30% |
| 105.5 | 110 | 6.95% | 0.02% | 91.36% | 0.00% | 0.31% | 1.37% |
| 105.2 | 115 | 6.72% | 0.01% | 91.48% | 0.00% | 0.32% | 1.47% |
| 105.2 | 120 | 6.50% | 0.00% | 91.45% | 0.00% | 0.31% | 1.73% |
| 105 | 125 | 6.08% | 0.02% | 92.13% | 0.00% | 0.31% | 1.46% |
| 105 | 130 | 6.12% | 0.02% | 92.04% | 0.00% | 0.31% | 1.50% | product content measured by GC Analysis

The following experiments were carried out in pressurized autoclaves. Accordingly, we carried out the condensation of butyraldehyde at varying temperatures and catalyst loadings at 40-60 psi and collected information on the reaction rate via periodic sampling. These experiments are detailed in tables 9-11. Collectively, these experiments demonstrate that the reaction rate and product selectivity can be significantly enhanced by carrying out the reaction at elevated temperature and pressure. Notably, by-product formation is minimized when the reaction was carried out for 2 hrs at 125° C. with 30 mol % catalyst loading with respect to the initial amount of butyraldehyde. Additionally, the catalyst loading may be lowered to 5 mol % without significant reduction in reaction rate/product selectivity.

TABLE 9

300 mL scale aldolization of butyraldehyde using 22 mol % DMA-OAC catalyst at 125° C.

| Time (min) | % n-HBu | % 2EH enal | % byproducts |
|---|---|---|---|
| 0 | 2.00 | 94.22 | 3.78 |
| 30 | 1.67 | 94.74 | 3.59 |
| 60 | 1.09 | 95.60 | 3.31 |
| 90 | 0.96 | 95.80 | 3.24 |
| 120 | 0.87 | 96.00 | 3.13 | product content measured by GC Analysis

TABLE 10

300 mL scale aldolization of butyraldehyde using 20 mol % DMA-OAC catalyst at various temperature after 2 hrs

| Temperature (° C.) | % n-HBu | % 2EH Enal | % byproducts |
|---|---|---|---|
| 160 | 1.24 | 90.42 | 8.34 |
| 140 | 0.85 | 94.52 | 4.63 |
| 125 | 0.87 | 96.18 | 2.95 |
| 100 | 1.72 | 93.69 | 4.59 |
| 80 | 3.71 | 85.61 | 10.68 |
| 30 | 11.08 | 65.16 | 23.76 | product content measured by GC Analysis

TABLE 11

300 mL scale aldolization of butyraldehyde using various DMA-OAC catalyst loading at 125° C. after 2 hours

| Cat. (mol %) | % n-HBu | % 2EH Enal | % byproducts |
|---|---|---|---|
| 40 | 0.66 | 94.97 | 4.37 |
| 35 | 0.69 | 95.28 | 4.03 |
| 30 | 0.60 | 96.59 | 2.81 |
| 25 | 0.73 | 95.72 | 3.55 |
| 22 | 0.86 | 96.00 | 3.14 |
| 20 | 0.87 | 96.18 | 2.95 |
| 15 | 1.02 | 95.81 | 3.17 |
| 10 | 1.27 | 95.34 | 3.39 |
| 5 | 2.58 | 93.45 | 3.97 | product content measured by GC Analysis

The invention has been described in detail with particular reference to certain embodiments thereof, but it will be understood that variations and modifications can be effected within the spirit and scope of the invention.

We claim:

1. A process for preparing an alkenal, comprising: 1) self-condensing an aliphatic aldehyde having at least 3 carbon atoms, in the presence of a catalyst comprising a dialkylammonium carboxylate salt, to produce the corresponding alkenal; and 2) washing said alkenal with dilute aqueous alkanoic acid to remove residual nitrogen from the product; wherein the residual nitrogen is about 1% or less nitrogen by CHN analysis.

2. A process for preparing an alkenal of the Formula (II)

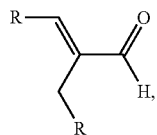
(II)

wherein R is chosen from phenyl, $C_1$-$C_{15}$ alkyl, or a group of the formula —$(CH_2)_n$-phenyl, wherein n is an integer of from 1 to 5,
which comprises: 1) contacting a compound of the Formula (I)

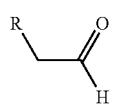
(I)

with a dialkylammonium carboxylate salt; and 2) washing said alkenal with dilute aqueous alkanoic acid to remove residual nitrogen from the product; wherein the residual nitrogen is about 1% or less nitrogen by CHN analysis.

3. The process of claim 2, wherein R is chosen from methyl, ethyl, propyl, butyl, pentyl, isopropyl, hexyl, septyl, octyl, nonyl, decyl, dodecyl, phenyl, benzyl, and a group of the formula —$CH_2CH_2$-Phenyl.

4. The process of claim 2, wherein the compound of Formula (I) is n-butyraldehyde.

5. The process of claim 2, wherein the compound of Formula (I) is pro pi on aldehyde.

6. The process of claim 2, wherein the compound of Formula (I) is octanal.

7. The process of claim 2, wherein the compound of Formula (I) is lauric aldehyde.

8. The process of claim 2, wherein the compound of Formula (I) is phenylacetaldehyde.

9. The process of claim 2, wherein the compound of Formula (I) is hydrocinnamaldehyde.

10. The process of claim 1, wherein the dialkylammonium carboxylate salt is chosen from salts of dimethylammonium acetate, dimethylamonium propionate, dimethylammonium trifluoroacetate, dimethylammonium 2-ethylhexanoate, diethylammonium acetate, diethylammonium propionate, diethylammonium trifluoroacetate, diethylammonium 2-ethylhexanoate, pyrrolidine acetate, pyrrolidine propionate, pyrollidine trifluoroacetate, pyrrolidine 2-ethylhexenoate, diisopropylammonium acetate, diisopropylammonim propionate, diisopropylammonium trifluoroacetate, diisopropylammonium 2-ethylhexanoate, and dibenzylammonium acetate.

11. The process of claim 2, wherein the dialkylammonium carboxylate salt is chosen from salts of dimethylammonium acetate, dimethylamonium propionate, dimethylammonium trifluoroacetate, dimethylammonium 2-ethylhexanoate, diethylammonium acetate, diethylammonium propionate, diethylammonium trifluoroacetate, diethylammonium 2-ethylhexanoate, pyrrolidine acetate, pyrrolidine propionate, pyrollidine trifluoroacetate, pyrrolidine 2-ethylhexenoate, diisopropylammonium acetate, diisopropylammonim propionate, diisopropylammonium trifluoroacetate, diisopropylammonium 2-ethylhexanoate, and dibenzylammonium acetate.

12. The process of claim 1, wherein the dialkylammonium carboxylate salt is chosen from diisopropylammonium acetate, diisopropylammonium propionate, diisopropylammonium trifluoroacetate, and diisopropylammonium 2-ethylhexanoate.

13. The process of claim 1, wherein the dialkylammonium carboxylate salt is diisopropylammonium acetate.

14. The process of claim 1, wherein the dialkylammonium carboxylate salt is dimethylammonium acetate.

15. The process of claim 2, wherein the process is conducted at a temperature of about 23° C. to about 160°.

16. The process of claim 1, further comprising the step of hydrogenation.

* * * * *